United States Patent [19]

Bergmin et al.

[11] Patent Number: 4,999,438

[45] Date of Patent: Mar. 12, 1991

[54] PROCESS FOR THE REDUCTION OF THE POLYMER PORTION IN THE DIMERIZATION OF KETENE

[75] Inventors: Renzo Bergmin, Raron; Wilhelm Quittmann, Visp; Josef Stoffel, Visperterminen, all of Switzerland

[73] Assignee: Lonza Ltd., Gampel, Switzerland

[21] Appl. No.: 460,659

[22] Filed: Jan. 3, 1990

[30] Foreign Application Priority Data

Jan. 5, 1989 [CH] Switzerland .............................. 30/89

[51] Int. Cl.$^5$ ............................................. C07D 305/12
[52] U.S. Cl. ..................................... 549/329; 549/328
[58] Field of Search ................................ 549/328, 329

[56] References Cited

U.S. PATENT DOCUMENTS

| | | | |
|---|---|---|---|
| 4,364,913 | 12/1982 | Katz et al. | 423/365 |
| 4,377,490 | 3/1983 | Shiraishi et al. | 428/442 |
| 4,389,386 | 6/1983 | Feit et al. | 502/330 |

FOREIGN PATENT DOCUMENTS

| | | | |
|---|---|---|---|
| 700218 | 3/1940 | Fed. Rep. of Germany | 549/529 |
| 1240847 | 11/1967 | Fed. Rep. of Germany | 549/529 |
| 1268625 | 6/1969 | Fed. Rep. of Germany | 549/529 |
| 1015080 | 12/1965 | United Kingdom | 549/329 |

OTHER PUBLICATIONS

*Chemical Abstracts:* 63:1708b, "Preparation of diketene," abstract of Neth. Appl. 6,408,804, (1965).
D. Bormann in Houben-Weyl, Methoden der Organischen Chemie (Methods of Organic Chemistry), vol. 7/4, pp. 226–228 (1968).
G. F. Pregaglia et al., Encyclopedia of Polymer Science and Technology, vol. 8, pp. 45–57, (1968 edn.).

*Primary Examiner*—Richard L. Raymond
*Assistant Examiner*—Mark W. Russell
*Attorney, Agent, or Firm*—Fisher, Christen & Sabol

[57] ABSTRACT

The polymer portion in the production of diketene by the dimerization of ketene obtained from acetic acid by pyrolysis is reduced by the addition of sulfur dioxide to the ketene gas or to the reaction medium.

3 Claims, No Drawings

PROCESS FOR THE REDUCTION OF THE POLYMER PORTION IN THE DIMERIZATION OF KETENE

BACKGROUND OF THE INVENTION

1. Field of the Invention

The invention relates to a process for the reduction of the polymer portion in crude diketene, which is produced by the catalytic pyrolysis of acetic acid and then the dimerization of the formed ketene.

2. Background Art

It is known that in the dimerization of ketene, besides the main product diketene, also resinous polymers and a ketene trimer are formed. [D. Borrmann in Houben-Weyl, Methoden der organischen Chemie (Methods of Organic Chemistry), vol. 7/4, 226, 228 (1968); and G. F. Pregaglia et al., Encyclop. Polymer. Sci. Techn., 8, 45 (1968)]. The formation of these ketene polymers, which are present in a portion of 8 to 10 percent in the crude diketene, means a loss of value in the dimerization of ketene and undesirable ballast or waste in the further processing.

Moreover, it is known that a portion of these polymers can be reduced by additives (inhibitors), such as, mineral acids, acetyl or benzoyl chloride, silicon tetrachloride, or sulfuryl chloride (German PS 700,218), or also by boron trifluoride, silicon tetrafluoride, tin(II) chloride, chloroacetic acid or p-toluene-sulfonic acid in the dimerization in a solvent (German PS 1,240,847). All of the above-cited known inhibitors are either protonic acids, metal or nonmetal halides or acid chlorides.

Another process for reduction of the polymer portion and for improvement of the storage stability of the diketene uses elementary sulfur in amounts of 0.1 to 2 percent by weight, relative to the amount of diketene (German PS 1,268,625). In this case, the sulfur is partially dissolved in the diketene but is mainly suspended therein.

But the inhibitors known so far exhibit a number of disadvantages. Thus, it has been shown that in the distillation of the diketene, metal compounds can even promote its polymerization, in other words, only shift the problem of resin formation. Also, for reasons of environmental protection, metal compounds as additives are undesirable, since in the end they must be eliminated as waste. On the other hand, acids and halogen compounds lead to corrosion of the apparatus and storage containers. The use of elemental sulfur has the disadvantage that, before the processing of the thus-stabilized diketene, a filtration and/or distillation is necessary for separation of the sulfur.

BROAD DESCRIPTION OF THE INVENTION

The object of the invention is to use an alternative, metal-free and halogen-free and nonprotonic acid inhibitor. According to the invention, the object is obtained by the invention process.

The invention involves a process for the reduction of the polymer portion in the dimerization of ketene, which is produced by catalytic pyrolysis of acetic acid. In the invention process, sulfur dioxide as the inhibitor is added in a concentration of 10 to 6000 ppm, preferably 100 to 2000 ppm, to the reaction medium of the dimerization or to the crude ketene gas before dimerization. The disadvantage that an additional solvent must be used, as in German PS 1,240,847, does not occur with the use of sulfur dioxide as the inhibitor. The inhibition process is suitable both for batch (Example 3) and continuous (Examples 1 and 2) dimerization of ketene. By the addition of the sulfur dioxide inhibitor, anionic polymerization chains are broken or traces of bases initiating polymerization are deactivated.

The process can be performed in an agitator vessel with a gas distribution tube or in a liquid-seal pump usually used for compressing the ketene gas or in countercurrent absorbers.

In a continuous process the amount of sulfur dioxide to be added is preferably controlled by assaying the sulfur concentration in the diketene product.

Analytically, the polymer portion is defined as the amount of the diketene product which remains as residue in vacuum evaporation (0.01 torr) at room temperature after 2 hours.

DETAILED DESCRIPTION OF THE INVENTION

Example 1 (Continuous Process)

Up to 550 ppm of sulfur dioxide (relative to the amount of the ketene gas) was fed into the suction side of a liquid-seal vacuum pump, which is used for compressing the crude ketene gas obtained by the catalytic pyrolysis of acetic acid. Pure diketene was used as the pump seal liquid. At a reaction temperature of 20° to 32° C., a reduction of the polymer portion of 1.5 to 9 percent resulted in comparison with an experimental procedure without sulfur dioxide (Table 1).

TABLE 1

| $SO_2$ Concentration, ppm | Polymer Portion, % | Dimerization Medium | Reaction Temp. (avg. value), °C. |
| --- | --- | --- | --- |
| 0 | 12.5 | Pure diketene | 24.4 |
| 150–250 | 10.5–11.0 | Pure diketene | 27.5 |
| 450–550 | 3.5–3.8 | Pure diketene | 27.5 |

Example 2 (Continuous Process)

In the same apparatus as described in Example 1, sulfur dioxide was introduced in such an amount that the stationary sulfur concentration in the dimerization medium was up to 2850 ppm of S. The observed reduction of the polymer portion was 3.2 to 6.4 percent (Table 2).

TABLE 2

| Sulfur Concentration In The Product, ppm | Polymer Portion, % | Dimerization Medium | Reaction Temp. (avg. value), °C. |
| --- | --- | --- | --- |
| 0 | 13.0 | Crude diketene | 23 |
| 530 | 9.8 | Crude diketene | 23 |
| 790 | 6.6 | Crude diketene | 23 |
| 900 | 8.1 | Crude diketene | 23 |
| 2850 | 9.5 | Crude diketene | 23 |

Example 3

Ketene gas, mixed with $SO_2$, was introduced for dimerization into 1 liter of diketene at 12°±2° C. in a 1.5-liter glass stirring device with a double jacket for cooling. At the end of the experiment, the polymer portion was determined as indicated above and was converted to the produced diketene (Table 3).

TABLE 3

| SO$_2$ Concentration, ppm | Polymer Portion, % | Dimerization Medium |
| --- | --- | --- |
| 0 | 14.5–15.3 | Pure diketene |
| 160 | 7.6–8.3 | Pure diketene |
| 84 | 8.7 | Pure diketene |
| 0 | 11.6 | Crude diketene |
| 1940 | 10.2 | Crude diketene |
| 750 | 9.0 | ⅔ Crude + ⅓ distilled diketene |

What is claimed is:

1. Process for the reduction of the polymer portion in the dimerization of ketene, which is produced by the catalytic pyrolysis of acetic acid, characterized in that sulfur dioxide as an inhibitor is added in an amount which provides a concentration of 10 to 6000 ppm in the reaction medium of the dimerization or in the crude ketene gas before dimerization.

2. Process according to claim 1 wherein the sulfur dioxide is added in an amount which provides a concentration of 100 to 2000 ppm in the reaction medium of the dimerization or in the crude ketene gas before dimerization.

3. Process according to claim 1 wherein the sulfur dioxide is added in an amount which provides a concentration of 450 to 550 ppm in the reaction medium of the dimerization or in the crude ketene gas before dimerization.

* * * * *

UNITED STATES PATENT AND TRADEMARK OFFICE
CERTIFICATE OF CORRECTION

PATENT NO. : 4,999,438

DATED : Mar. 12, 1991

INVENTOR(S) : Renzo BERGAMIN et al.

It is certified that error appears in the above-identified patent and that said Letters Patent is hereby corrected as shown below:

On the title page, item [19] "Bergmin et al" should read --Bergamin et al--; and item [75] Inventors: "Renzo Bergmin" should read --Renzo Bergamin--.

Signed and Sealed this

Fourteenth Day of July, 1992

Attest:

DOUGLAS B. COMER

*Attesting Officer*  *Acting Commissioner of Patents and Trademarks*